United States Patent
Koike

(10) Patent No.: US 7,510,728 B2
(45) Date of Patent: Mar. 31, 2009

(54) SOLID PREPARATIONS

(75) Inventor: Masahiko Koike, Toyonaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 625 days.

(21) Appl. No.: 10/398,434

(22) PCT Filed: Oct. 5, 2001

(86) PCT No.: PCT/JP01/08785

§ 371 (c)(1), (2), (4) Date: Apr. 2, 2003

(87) PCT Pub. No.: WO02/30400

PCT Pub. Date: Apr. 18, 2002

(65) Prior Publication Data

US 2004/0033258 A1    Feb. 19, 2004

(30) Foreign Application Priority Data

Oct. 6, 2000 (JP) .............................. 2000-313105
Oct. 6, 2000 (JP) .............................. 2000-313106

(51) Int. Cl.
  A61K 9/20  (2006.01)
  A61K 9/28  (2006.01)
  A61K 9/30  (2006.01)
  A61K 9/32  (2006.01)
  A61K 9/36  (2006.01)

(52) U.S. Cl. .................... 424/464; 424/465; 424/474; 424/475; 424/479; 424/480; 424/482

(58) Field of Classification Search ............. None
See application file for complete search history.

(56) References Cited

U.S. PATENT DOCUMENTS 5,401,514 A * 3/1995 Juch et al. ............ 424/465
5,785,984 A * 7/1998 Kurihara et al.
6,559,188 B1 * 5/2003 Gatlin et al. ............ 514/641
6,589,554 B1 * 7/2003 Mizumoto et al.

FOREIGN PATENT DOCUMENTS

| | | |
|---|---|---|
| EP | 0839526 | 5/1998 |
| EP | 0922464 | 6/1999 |
| JP | 4327529 | 11/1992 |
| JP | 6116138 | 4/1994 |
| JP | 7285868 | 10/1995 |
| JP | 10114655 | 5/1998 |
| JP | 10236947 | 9/1998 |
| JP | 11035486 | 2/1999 |
| JP | 11092402 | 4/1999 |
| JP | 11228450 | 8/1999 |
| JP | 2000-239186 A | 9/2000 |
| JP | 2000273039 | 10/2000 |
| JP | 2001058944 | 3/2001 |
| WO | WO 89/05640 | 6/1989 |
| WO | WO 96/02237 | 2/1996 |

* cited by examiner

Primary Examiner—Humera N Sheikh
(74) Attorney, Agent, or Firm—Foley & Lardner LLP

(57) ABSTRACT

In a solid pharmaceutical preparation containing 1) a basic medicinal component having an unpleasant taste; 2) a saccharide; 3) a polyanionic polymer; 4) a corrigent; and 5) carboxymethylcellulose, the unpleasant taste of the basic medicinal component having an unpleasant taste can be satisfactorily masked and excellent properties such as quick disintegration, appropriate preparation strength and high storage stability over a long period of time, etc., can be achieved. Further, a quickly disintegrating solid pharmaceutical preparation containing a medicinal component, a sugar alcohol and carboxymethylcellulose has excellent properties such as quick disintegration, appropriate preparation strength, high storage stability over a long period of time, etc.

4 Claims, No Drawings

SOLID PREPARATIONS

This application is the National Phase filing of International Patent Application No. PCT/JP01/08785, filed Oct. 5, 2001.

TECHNICAL FIELD

The present invention relates to a solid pharmaceutical preparation comprising 1) a basic medicinal component having an unpleasant taste, 2) a saccharide, 3) a polyanionic polymer, 4) a corrigent and 5) carboxymethylcellulose; and a manufacturing process thereof.

Further, the present invention relates to a quickly disintegrating solid pharmaceutical preparation, i.e., a solid pharmaceutical preparation quickly disintegrating in the presence of saliva in the oral cavity, in the presence of a small amount of water, or in stomach, in particular, to that useful as a solid pharmaceutical preparation quickly disintegrating in the oral cavity.

BACKGROUND ART

In solid pharmaceutical preparations containing a basic medicinal component having an unpleasant taste, methods for masking the unpleasant taste are disclosed, for example, in the following publications.

JP 02-502729 A discloses "a pharmaceutical granule composition comprising cimetidine and, as a granulating and taste-masking agent, an ester of a polyhydroxy compound, and, optionally, a palatable pharmaceutically acceptable emulsifier."

JP 06-116138 A discloses "a composition for an oral pharmaceutical preparation comprising (a) a complex formed by dispersing or dissolving an unpleasantly tasting basic drug and a polymer compound soluble in stomach in a substance having a low melting point, (b) 10 to 70% by weight of a sugar alcohol and (c) 0.1 to 7% by weight of an basic oxide."

JP 10-236947 A discloses "a granular pharmaceutical preparation obtained from a process for manufacturing a pharmaceutical preparation bulk comprising the steps of:

(1) melting and granulating a mixture comprising a drug having a physiological activity and polyethylene glycol;

(2) re-melting and re-granulating said granulated granules after addition of an excipient."

JP 11-228450 A discloses "an oral composition comprising a basic drug having an unpleasant taste and an anionic high-molecular weight substance, in which the unpleasant taste is masked."

On the other hand, recently, a solid pharmaceutical preparation disintegrating and/or being dissolved quickly in the oral cavity has been developed for patients with difficulty in swallowing drugs, aged persons and children as a dosage form which can be easily ingested.

Such solid pharmaceutical preparations, for example, are described in the following publication.

JP 10-114655 A disclosed "a solid pharmaceutical preparation comprising a therapeutically effective amount of at least one kind of a drug, at least one kind of a neutral or basic additive and a disintegrant."

In the solid pharmaceutical preparations described in the above known publications, it cannot be said that masking of an unpleasant taste of a medicinal component is sufficient and their disintegration property and preparation strength are satisfactory. Therefore, it is desired to develop a solid pharmaceutical preparation having excellent properties such as adequate masking of an unpleasant taste of a basic medicinal component having the unpleasant taste (hereinafter, sometimes abbreviate to a basic medicinal component), as well as a quick disintegration property and appropriate preparation strength, etc.

In addition, since a disintegration property and preparation strength of the solid pharmaceutical preparations described in the above known publications are unsatisfactory, it is desired to develop a solid pharmaceutical preparation having a quick disintegration property and appropriate preparation strength.

DISCLOSURE OF THE INVENTION

The present inventor has studied incorporation of a basic medicinal component having an unpleasant taste into a pharmaceutical preparation. As a result, the present inventor has found that a solid pharmaceutical preparation in which unpleasant taste of the basic medicinal component is fully masked can be obtained by using a combination of a saccharide, a polyanionic polymer, a corrigent and carboxymethylcellulose.

Further, the present inventor has found an industrially advantageous manufacturing process of the above solid pharmaceutical preparation.

The present inventor has further continued to study based on these findings and, finally, completed the present invention.

That is, the present invention relates to:

(1) A solid pharmaceutical preparation comprising 1) a basic medicinal component having an unpleasant taste, 2) a saccharide, 3) a polyanionic polymer, 4) a corrigent, and 5) carboxymethylcellulose;

(2) The pharmaceutical preparation according to the above (1), which is a quickly disintegrating solid pharmaceutical preparation;

(3) The pharmaceutical preparation according to the above (2), which is a solid pharmaceutical preparation quickly disintegrating in the oral cavity;

(4) The pharmaceutical preparation according to the above (1), which is in the form of a tablet;

(5) The pharmaceutical preparation according to the above (1), wherein the basic medicinal component having an unpleasant taste is pioglitazone hydrochloride;

(6) The pharmaceutical preparation according to the above (1), wherein the saccharide is a sugar alcohol;

(7) The pharmaceutical preparation according to the above (6), wherein the sugar alcohol is mannitol, erythritol, trehalose or xylitol;

(8) The pharmaceutical preparation according to the above (6), wherein the sugar alcohol is mannitol;

(9) The pharmaceutical preparation according to the above (1), wherein the polyanionic polymer is sodium carboxymethylcellulose or sodium alginate;

(10) The pharmaceutical preparation according to the above (1), wherein the polyanionic polymer is sodium carboxymethylcellulose;

(11) The pharmaceutical preparation according to the above (1), wherein the corrigent is sodium glutamate, sodium 5'-inosinate, sodium 5'-guanylate or sodium aspartate;

(12) The pharmaceutical preparation according to the above (1), wherein the corrigent is sodium glutamate;

(13) The pharmaceutical preparation according to the above (1), wherein the saccharide is incorporated into the preparation in an amount of 5 to 97 parts by weight based on 100 parts by weight of the solid pharmaceutical preparation;

(14) The pharmaceutical preparation according to the above (1), wherein the polyanionic polymer is incorporated into the preparation in an amount of 1 to 50 parts by weight based on 100 parts by weight of the solid pharmaceutical preparation;

(15) The pharmaceutical preparation according to the above (1), wherein the corrigent is incorporated into the preparation in an amount of 0.1 to 15 parts by weight based on 100 parts by weight of the solid pharmaceutical preparation;

(16) A process for manufacturing a solid pharmaceutical preparation, which comprises the steps of mixing a composition comprising a basic medicinal component having an unpleasant taste, a saccharide and a polyanionic polymer, and a composition comprising a saccharide and a corrigent, and then compression-molding the resultant mixture; and the like.

Further, the present inventor has studied a quickly disintegrating solid pharmaceutical preparation and has found that a solid pharmaceutical preparation having a quick disintegration property and appropriate preparation strength can be obtained by using a combination of a sugar alcohol and carboxymethylcellulose.

Furthermore, the present inventor has found that a solid pharmaceutical preparation having practically acceptable hardness without any problem in a quick disintegration property and productivity can be obtained by using carboxymethylcellulose even in dry compression at low compression force.

The present inventor has further continued to study based on these findings and completed the present invention.

That is, the present invention also relates to:

(17) A quickly disintegrating solid pharmaceutical preparation comprising a medicinal component, a sugar alcohol, and carboxymethylcellulose;

(18) The pharmaceutical preparation according to the above (17), which is a solid pharmaceutical preparation quickly disintegrating in the oral cavity;

(19) The pharmaceutical preparation according to the above (17), which is in the form of a tablet;

(20) The pharmaceutical preparation according to the above (17), wherein the sugar alcohol is mannitol, erythritol, trehalose or xylitol;

(21) The pharmaceutical preparation according to the above (17), wherein the sugar alcohol is mannitol;

(22) The pharmaceutical preparation according to the above (17), wherein the sugar alcohol is incorporated into the preparation in an amount of 5 to 97 parts by weight based on 100 parts by weight of the quickly disintegrating solid pharmaceutical preparation;

(23) The pharmaceutical preparation according to the above (17), wherein the sugar alcohol is incorporated into the preparation in an amount of 44 to 90 parts by weight based on 100 parts by weight of the quickly disintegrating solid pharmaceutical preparation;

(24) The pharmaceutical preparation according to the above (17), wherein carboxymethylcellulose is incorporated into the preparation in an amount of 1 to 40 parts by weight based on 100 parts by weight of the quickly disintegrating solid pharmaceutical preparation;

(25) The pharmaceutical preparation according to the above (17), which contains pioglitazone hydrochloride as the medicinal component;

(26) The pharmaceutical preparation according to the above (17), which contains manidipine hydrochloride as the medicinal component;

(27) The pharmaceutical preparation according to the above (17), which contains voglibose as the medicinal component;

(28) The pharmaceutical preparation according to the above (17), which contains candesartan cilexetil as the medicinal component;

(29) The pharmaceutical preparation according to the above (17), which contains hydrochlorothiazide as the medicinal component;

(30) The pharmaceutical preparation according to the above (17), which further comprises a polyanionic polymer;

(31) The pharmaceutical preparation according to the above (17), which further comprises a corrigent;

(32) The pharmaceutical preparation according to the above (17), which further comprises a polyanionic polymer and a corrigent;

(33) A process for manufacturing a quickly disintegrating solid pharmaceutical preparation which comprises the steps of mixing a medicinal component, a sugar alcohol and carboxymethylcellulose, and compression-molding the resultant mixture; and the like.

Hereinafter, the "solid pharmaceutical preparation comprising 1) a basic medicinal component having an unpleasant taste, 2) a saccharide, 3) a polyanionic polymer, 4) a corrigent, and 5) carboxymethylcellulose" and a manufacturing process thereof will be described in detail.

"A basic medicinal component having an unpleasant taste" may be in any form such as solid, crystalline, oil or solution in so far as it is basic and has an unpleasant taste (such as bitter taste, hot taste, pungent taste, etc.).

Examples of the basic medicinal component include nourishing and health-promoting agents, antipyretic analgesic antiphlogistic agents, antidepressants, antispasmodics, cerebral metabolism improving agents, sympathomimetic agents, gastrointestinal function conditioning agents, antiulcer drugs, antitussive-expectorants, antiemetic drugs, antiallergic agents, agents for dental and oral use, antihistamines, cardiotonics, antiarrhythmics, hypotensors, vasoconstrictors, coronary vasodilators, antibiotics, agents for treating diabetes, alkaloidal narcotics, etc. Two or more of these basic medicinal components may be mixed and used at an appropriate ratio, unless such mixture adversely influences the pharmacological activity of each basic medicinal component. Further a medicinal component other than the above may also be mixed and used at an appropriate ratio.

Examples of the nourishing and health-promoting agents include vitamin $B_1$ (e.g., dibenzoylthiamine, fursultiamine hydrochloride, etc.), vitamin $B_6$ (e.g., pyridoxine hydrochloride, etc.), etc.

Examples of the antipyretic analgesic antiphlogistic agent include diphenhydramine hydrochloride, diphenhydramine salicylate, diphenhydramine tannate, methylephedrine hydrochloride, phenylpropanolamine hydrochloride, lysozyme chloride, etc.

Examples of the antidepressant include imipramine, maprotiline hydrochloride, amphetamine, etc.

Examples of the antispasmodic include diphenhydramine hydrochloride, papaverine hydrochloride, meclizine hydrochloride, etc.

Examples of the cerebral metabolism improving agent include meclofenoxate hydrochloride, donepezil hydrochloride, etc.

Examples of the sympathomimetic agent include phenylephrine hydrochloride, ephedrine hydrochloride, methoxyphenamin hydrochloride, Norepinephrine, methoxamine, isoproterenol hydrochloride, etc.

Examples of the gastrointestinal function conditioning agent include berberine chloride, cetraxate hydrochloride, etc.

Examples of the antiulcer drug include ranitidine hydrochloride, cimetidine, famotidine, etc.

Examples of the antitussive-expectorant include cloperastine hydrochloride, dextromethorphan, noscapine hydrochloride, phenylpropanolamine hydrochloride, bromhexine hydrochloride, ambroxol hydrochloride, etc.

Examples of the antiemetic include difenidol hydrochloride, etc.

Examples of the antiallergic agent include isothipendyl hydrochloride, promethazine hydrochloride, promethazine methylenedisalicylate, clemastine fumarate, chlorpheniramine maleate, ketotifen fumarate, alimemazine tartrate, azelastine hydrochloride, emedastine difumarate, epinastine hydrochloride, amlexanox, Ibudilast, oxatomide, etc.

Examples of the agent for dental and oral use include chlorhexidine hydrochloride, etc.

Examples of the antihistamine include diphenhydramine hydrochloride, isothipendyl hydrochloride, dl-chlorpheniramine maleate, etc.

Examples of the cardiotonic include caffeine, digoxin, etc.

Examples of the antiarrhythmic include procainamide hydrochloride, propranolol hydrochloride, etc.

Examples of the hypotensor include delapril hydrochloride, hydralazine hydrochloride, labetalol hydrochloride, etc.

Examples of the vasoconstrictor include phenylephrine hydrochloride, etc.

Examples of the coronary vasodilator include carbocromen hydrochloride, verapamil hydrochloride, etc.

Examples of the antibiotic include pivmecillinam hydrochloride, cefotiam hexetil hydrochloride, erythromycin, clarithromycin, kitasamycin, josamycin, midecamycin, roxithromycin, azithromycin, etc.

Examples of the agent for treating diabetes include insulin resistance improving agent such as pioglitazone hydrochloride, rosiglitazone maleate, etc.

Examples of the alkaloidal narcotic include morphine hydrochloride, morphine sulfate, oxycodone hydrochloride, opium alkaloid hydrochlorides, cocaine hydrochloride, etc.

When the above-mentioned wide variety of basic medicinal components form salts, they may also be used as free forms thereof. In addition, the above-mentioned wide variety of basic medicinal component are free forms which can form salts, they may also be used in the form of salts thereof. Such salts include pharmaceutically acceptable salts such as salts formed with inorganic acids, salts formed with organic acids and salts formed with acidic amino acids. In some cases, the above free form is basic, while its salt is not basic. Such a salt is also included in the basic medicinal component of the present invention.

Preferred examples of the salt formed with an inorganic acid include salts with hydrochloric acid, hydrobromic acid, nitric acid, sulfuric acid, and phosphoric acid, etc.

Preferred examples of the salt formed with an organic acid include salts with formic acid, acetic acid, trifluoroacetic acid, fumaric acid, oxalic acid, tartaric acid, maleic acid, citric acid, succinic acid, malic acid, methansulfonic acid, benzenesulfonic acid, p-toluenesulfonic acid, etc.

Preferred examples of the salt formed with an acidic amino acid include salts with aspartic acid, glutamic acid, etc.

The above-described basic medicinal component may be that diluted with a diluent generally used in medical and food fields, etc. Further, the basic medicinal component may be coated with a coating agent as described hereinafter.

Preferably, the above-described basic medicinal component is an agent for treating diabetes, more preferably, it is an insulin resistance improving agent, and specifically preferred is pioglitazone hydrochloride.

The content of the basic medicinal component in the solid pharmaceutical preparation of the present invention varies according to a particular kind of the component, dose thereof, etc. However, normally, the component is incorporated in the preparation in an amount of 0.01 to 60 parts by weight, preferably 0.01 to 40 parts by weight based on 100 parts by weight of the solid pharmaceutical preparation.

Examples of the saccharide include sugar, starch sugar, lactose, honey, sugar alcohols, etc. Two or more thereof may be mixed and used at an appropriate ratio.

Examples of the sugar include white sugar, coupling sugar, fructo-oligosaccharide, palatinose, etc.

Examples of the starch sugar include glucose, maltose, powdered starch syrup, starch syrup, fructose, etc.

Examples of the lactose include lactose, isomerized lactose (lactulose), reduced lactose (lactitol), etc.

Examples of the honey include various honey generally used as an edible product.

Examples of the sugar alcohol include sorbitol, mannitol, maltitol, hydrogenated glucose syrup, xylitol, reduced palatinose, erythritol, trehalose, etc.

Preferably, the saccharide is a sugar alcohol, in particular, mannitol, erythritol, trehalose or xylitol. Among them, mannitol is preferred.

Normally, the content of the saccharide in the solid pharmaceutical preparation of the present invention is 5 to 97 parts by weight, preferably 10 to 90 parts by weight, more preferably 44 to 90 parts by weight based on 100 parts by weight of the solid pharmaceutical preparation.

Further, the unpleasant taste of the basic medicinal component can be masked more effectively by using the saccharide in an amount of 1 to 20 parts by weight, preferably 2 to 10 parts by weight based on 1 part by weight of a basic medicinal component having an unpleasant taste.

Further, the solid pharmaceutical preparation having an excellent disintegration property can be obtained by using the saccharide in an amount of 1 to 100 parts by weight, preferably 2 to 50 parts by weight based on 1 part by weight of carboxymethylcellulose.

Examples of the polyanionic polymer include sodium carboxymethylcellulose, sodium alginate, etc. They may be mixed and used at an appropriate ratio.

As sodium carboxymethylcellulose to be used herein, preferred is that having a degree of etherification of 2 or less, more preferably 1.5 or less. Specific example thereof includes Sunrose F (trade name, GOTOKU CHEMICAL COMPANY LTD.), etc.

Sodium alginate is a sodium salt of alginic acid composed of a polymer of D-mannuronic acid and L-guluronic acid and specific example thereof includes Duck Algin (trade name, KIBUN FOOD CHEMIFA Co., Ltd.), etc.

The polyanionic polymer is preferably sodium carboxymethylcellulose.

Normally, the content of the polyanionic polymer in the solid pharmaceutical preparation of the present invention is 1 to 50 parts by weight, preferably 2 to 30 parts by weight based on 100 parts by weight of the solid pharmaceutical preparation.

Further, the unpleasant taste of the basic medicinal component can be masked more effectively by using the polyanionic polymer in an amount of 0.05 to 5 parts by weight, preferably 0.1 to 2 parts by weight based on 1 part by weight of the basic medicinal component having an unpleasant taste.

Examples of the corrigent include salts of organic acids for modifying a taste such as sodium glutamate, sodium 5'-inosinate, sodium 5'-guanylate, sodium aspartate, etc. Two or more thereof may be mixed and used at an appropriate ratio.

The especially preferred corrigent is sodium glutamate. Normally, the content of the corrigent in the solid pharmaceutical preparation of the present invention is 0.1 to 15 parts by weight, preferably 0.2 to 10 parts by weight based on 100 parts by weight of the solid pharmaceutical preparation.

It is preferred to employ the content within the above-described range because an excess content of the corrigent strengthens the taste of the corrigent itself upon ingestion, while the unpleasant taste of "a basic medicinal component having an unpleasant taste" is getting to be masked as increasing a content of the corrigent in the solid pharmaceutical preparation.

Further, the unpleasant taste of the basic medicinal component can be masked more effectively by using the corrigent in an amount of 0.01 to 2 parts by weight, preferably 0.05 to 1 parts by weight based on 1 part by weight the basic medicinal component having an unpleasant taste.

Carboxymethylcellulose used in the present invention means an acidic high-molecular weight electrolyte cellulose ether whose cellulosic hydroxy group is partially carboxymethylated. Such carboxymethylcellulose is easily commercially available and specific example includes NS-300 (GOTOKU CHEMICAL COMPANY LTD.).

Normally, the content of carboxymethylcellulose in the solid pharmaceutical preparation of the present invention is 1 to 40 parts by weight, preferably 2 to 30 parts by weight based on 100 parts by weight of the solid pharmaceutical preparation.

It is preferred to employ the content of the carboxymethylcellulose within the above-described range in case of the solid pharmaceutical preparation quickly disintegrating in the oral cavity because an excess content results in a solid pharmaceutical preparation having powdery mouthfeel upon ingestion, while a disintegration property in the oral cavity of the solid pharmaceutical preparation is increased as increasing a content of carboxymethylcellulose in the solid pharmaceutical preparation.

Examples of dosage forms of the solid pharmaceutical preparation of the present invention include tablets, granules, fine granules, pills, etc. Among them, tablets are preferred.

The solid pharmaceutical preparation of the present invention is preferably a quickly disintegrating solid pharmaceutical preparation. The quickly disintegrating property used herein means such a property that the solid pharmaceutical preparation disintegrates within a short period of time (such as about 5 to 90 seconds) in the oral cavity, in water or in stomach. While the disintegration time of the quickly disintegrating solid pharmaceutical preparation in the oral cavity (the time required for complete disintegration by saliva in the oral cavity of a healthy male or female adult) varies according to particular dosage form, size, etc., of the solid pharmaceutical preparation, in case that the solid pharmaceutical preparations is in the form of a tablet, for example, it is usually 5 to 90 seconds, preferably 5 to 60 seconds, more preferably 5 to 30 seconds.

The solid pharmaceutical preparation of the present invention is, more preferably, the solid pharmaceutical preparation quickly disintegrating in the oral cavity. The solid pharmaceutical preparation quickly disintegrating in the oral cavity is useful in prevention and treatment of various diseases as a preparation easy to ingest for patients having a difficulty in swallowing a drug, elderly persons, or children, and as a preparation safe in an emergency for general adults.

Hardness of the solid pharmaceutical preparation of the present invention (that measured by a tablet hardness tester) is, preferably about 15 to 200 N, more preferably about 15 to 150 N.

The solid pharmaceutical preparation of the present invention may contain additives conventionally used in the field of pharmaceuticals. Examples of such additives include excipients, disintegrants, binders, acidulants, foaming agents, artificial sweeteners, flavoring agents, lubricants, coloring agents, stabilizers, pH control agents, surfactants, etc. Two or more thereof may be mixed and used at an appropriate ratio. In addition, these additives can be used in an amount conventionally used in the field of pharmaceuticals.

Examples of the excipient include starches such as corn starch, potato starch, wheat starch, rice starch, partial α starch, α starch, starch treated by a perforated centrifuge; anhydrous calcium phosphate, precipitated calcium carbonate, calcium silicate, light anhydrous silicic acid, etc. Examples of light anhydrous silicic acid includes Sylysia 320 (trade name, Fuji Silysia Chemical Ltd.), Aerosil 200 (trade name, Nippon Aerosil Co., Ltd.), etc.

Examples of the disintegrant include carboxymethylcellulose, calcium carboxymethylcellulose, sodium carboxymethyl starch, croscarmellose sodium, crospovidone, low-substituted hydroxypropyl cellulose, hydroxypropyl starch, etc. Specific examples of the disintegrants include carboxymethylcellulose (GOTOKU CHEMICAL COMPANY LTD.); crospovidone [manufactured by ISP Inc. (U.S.), BASF (Germany)]; croscarmellose sodium (FMC-Asahi Kasei Corporation); calcium carboxymethylcellulose (GOTOKU CHEMICAL COMPANY LTD.); sodium carboxymethyl starch (such as Matsutani Chemical Industry Co., Ltd., Kimura Industry Co., Ltd.); low-substituted hydroxypropyl cellulose whose hydroxypropoxyl group content is 5 to 16% by weight such as low-substituted hydroxypropyl cellulose LH11, LH21, LH31, LH22, LH32, LH20, LH30, LH32, LH33 (all manufactured by Shin-Etsu Chemical Co., Ltd.), etc. The amount of the disintegrant used is preferably 0.5 to 25 parts by weight, more preferably 1 to 15 parts by weight based on 100 parts by weight of the solid pharmaceutical preparation.

Examples of the binder include crystalline cellulose, hydroxypropyl cellulose, hydroxypropylmethyl cellulose, polyvinyl pyrrolidone, powdered gum arabic, gelatin, pullulan, etc. Specific examples of the crystalline cellulose include Ceolus KG801, Avicel PH101, PH102, PH301, PH302, PH-F20, and Avicel RC-A591NF (all trade name, Asahi Kasei Corporation) and also include so-called microcrystalline cellulose, etc. The amount of the binder used is preferably 0.1 to 50 parts by weight, more preferably 0.5 to 40 parts by weight based on 100 parts by weight of the solid pharmaceutical preparation.

Examples of the acidulant include citric acid, tartaric acid, malic acid, ascorbic acid, etc.

Examples of the foaming agent include sodium hydrogen carbonate, sodium carbonate, etc.

Examples of the artificial sweetener include saccharin sodium, dipotassium glycyrrhizinate, aspartame, stevioside, thaumatin, acesulfame, etc.

Examples of the flavoring agent include lemon oil, orange oil, grapefruit oil, strawberry oil, menthol, peppermint oil, etc.

Examples of the lubricant include magnesium stearate, sucrose fatty acid ester, polyethyleneglycol, talc, stearic acid, sodium stearyl fumarate, etc.

Examples of the coloring agent include food colors such as food yellow No. 5, food red No. 2 and food blue No. 2, edible lake pigments, iron sesquioxide, etc.

Examples of the stabilizer include disodium edetate, tocopherol, cyclodextrin, etc.

Examples of the pH control agent include citrate, phosphate, carbonate, tartarate, fumarate, acetate, salt formed with amino acid, etc.

Examples of the surfactant include sodium laurylsulfate, polysorbate 80, hydrogenated oil, polyoxyethylene(160) polyoxypropylene(30)glycol, etc.

A particle size of the above-described additives, is not specifically limited, but preferably not more than 500 μm which causes little or no roughness in the oral cavity.

The solid pharmaceutical preparation of the present invention can be manufactured, for example, according to a conventional method in the field of pharmaceuticals, by mixing a basic medicinal component having an unpleasant taste, a saccharide, a polyanionic polymer, a corrigent and carboxymethylcellulose optionally together with the above-described additives and then compression-molding the resultant mixture.

The mixing (including granulation, drying, milling, etc.) is carried out by using a pharmaceutical machine such as a high-speed agitating granulator (FM-VG-10; manufactured by Powrex Corporation), an all-round kneader (manufactured by Hata Tekkosho, Co., Ltd.), a fluidized bed granulation dryer (LAB-1FD-3S, FD-3SN; manufactured by Powrex Corporation), a box vacuum dryer (manufactured by Kusunoki Machinery Co., Ltd.), a screen mill (P-3;SHOWA GIKEN INDUSTRIAL CO., LTD.), etc.

Compression-molding is, when the solid pharmaceutical preparation is in the form of a tablet, carried out by compressing at force of 5 to 35 kN/cm$^2$, using a tableting machine such as a single-punch tableting machine (manufactured by KIKUSUI SEISAKUSHO LTD.), a rotary tableting machine (manufactured by KIKUSUI SEISAKUSHO LTD.), etc.

For manufacturing the solid pharmaceutical preparation of the present invention, the following processes (1) to (3) can be employed because the solid pharmaceutical preparation having an excellent disintegration property can be obtained. In the solid pharmaceutical preparation manufactured by these processes, since a strong binding power among particles in the preparation brought about by a polyanionic polymer is reduced, a disintegration property of the preparation is improved.

(1) A process by mixing a composition comprising a basic medicinal component having an unpleasant taste, a saccharide and a polyanionic polymer (hereinafter referred to as composition A) and a composition comprising a saccharide, a corrigent and carboxymethylcellulose (hereinafter referred to as composition B), and then compression-molding the resultant mixture (the saccharides contained in composition A and B may be the same or different);

(2) A process by mixing a composition comprising a basic medicinal component having an unpleasant taste, a saccharide, a polyanionic polymer and a corrigent (hereinafter referred to as composition C) and a composition containing saccharide and carboxymethylcellulose (hereinafter referred to as composition D), and then compression-molding the resultant mixture (the saccharides contained in composition C and D may be the same or different);

(3) A process by mixing a composition comprising a basic medicinal component having an unpleasant taste, saccharide and a polyanionic polymer (hereinafter referred to as composition E) and a composition comprising a saccharide and carboxymethylcellulose (composition D), and then compression-molding the resultant mixture (the saccharides contained in composition E and D may be the same or different).

Each of the above-described compositions may contain the above-mentioned additives. The content of each component in these compositions is determined appropriately so that each content of the components in the desired solid pharmaceutical preparation may become the above-mentioned content. In addition, in the above processes (1) to (3), the above-mentioned additives may be added upon compression-molding.

Examples of the preferred manufacturing process of the solid pharmaceutical preparation of the present invention include the following processes (1a) to (3a).

(1a) A basic medicinal component having an unpleasant taste, a saccharide and a polyanionic polymer are mixed, optionally together with the above-mentioned additives, in an appropriate mixer and the resultant mixture is granulated.

On the other hand, a saccharide, a corrigent and carboxymethylcellulose are mixed, optionally together with the above-mentioned additives, in an appropriate mixer and the resultant mixture is granulated.

These two kinds of granules obtained are mixed, optionally together with the above-mentioned additives, followed by tableting by an appropriate tableting machine to obtain tablets.

(2a) A basic medicinal component having an unpleasant taste, a saccharide, a polyanionic polymer and a corrigent are mixed, optionally together with above-mentioned additives, in an appropriate mixer and the resultant mixture is granulated.

On the other hand, a saccharide and carboxymethylcellulose are mixed, optionally together with the above-mentioned additives, in an appropriate mixer and the resultant mixture is granulated.

These two kinds of granules obtained are mixed, optionally together with the above-mentioned additives, followed by tableting by an appropriate tableting machine to obtain tablets.

(3a) A basic medicinal component having an unpleasant taste, a saccharide and a polyanionic polymer are mixed, optionally together with the above-mentioned additives, in an appropriate mixer and the resultant mixture is granulated.

On the other hand, a saccharide and carboxymethylcellulose are mixed, optionally together with the above-mentioned additives, in an appropriate mixer and the resultant mixture is granulated.

These two kinds of granules obtained are mixed together with a corrigent and optionally the above-mentioned additives, followed by tableting by an appropriate tableting machine to obtain tablets.

In the above processes (1a) to (3a), granulation is carried out by compressing and granulating the mixture in dry granulation with, for example, a slug process or a roller compactor process; by wet granulation with a solvent (e.g., water, acetone, ethyl alcohol, propyl alcohol, a mixture thereof, etc.) in which the above-mentioned binder is dissolved or dispersed as needed; etc.

Further, the present invention relates to a process for manufacturing the solid pharmaceutical preparation which comprises mixing a composition comprising a basic medicinal component having an unpleasant taste, a saccharide and a polyanionic polymer, and a composition comprising a saccharide and a corrigent, and then compression-molding the resultant mixture.

This manufacturing process is carried out according to the same manner as the above processes (1) to (3), preferably the above (1a) to (3a) except that carboxymethylcellulose is not used. The solid pharmaceutical preparation having an excellent disintegration property can be obtained by using these processes. In addition, in the solid pharmaceutical preparations manufactured by these processes, since binding power among particles in the preparation brought about by a polyanionic polymer is reduced, a disintegration property of the preparation is improved.

The shape of the solid pharmaceutical preparation of the present invention is not specifically limited and may be any of the form of round, caplet, doughnut, oblong, etc. Further, the preparation may be a multi-layer tablet, a nucleated tablet, etc.

The solid pharmaceutical preparation may be coated with a coating agent and may have a mark or a letter for identification, and further a cleavage line for partition.

Examples of a coating base material included sugar coating base materials, water-soluble film coating base materials, enteric film coating base materials, sustained-release film coating base materials, etc.

As the sugar coating base material, white sugar is used, and one or more materials selected from talc, precipitated calcium carbonate, gelatin, gum arabic, pullulan, carnauba wax, etc., may be used together.

Examples of the water-soluble film coating base material include cellulosic polymers such as hydroxypropyl cellulose, hydroxypropylmethyl cellulose, hydroxyethyl cellulose, methylhydroxyethyl cellulose; synthetic polymers such as polyvinylacetal diethylaminoacetate, aminoalkyl methacrylate copolymer E (Eudragit E (trade name), Rohm Pharma), polyvinyl pyrrolidone; polysaccharides such as pullulan, etc., and the like Examples of the enteric film coating base materials include cellulosic polymers such as hydroxypropylmethylcellulose phthalate, hydroxypropylmethyl cellulose acetate succinate, carboxymethylethyl cellulose, cellulose acetate phthalate; acrylic polymers such as methacrylate copolymer L (Eudragit L (trade name), Rohm Pharma), methacrylate copolymer LD (Eudragit L-30D55 (trade name), Rohm Pharma), methacrylate copolymer S (Eudragit S (trade name), Rohm Pharma); natural products such as shellac, etc.

Examples of the sustained-release film coating base materials include cellulosic polymers such as ethyl cellulose; acrylic polymers such as aminoalkyl methacrylate copolymer RS (Eudragit RS (trade name), Rohm Pharma), suspension of a copolymer based on ethyl acrylate and methyl methacrylate (Eudragit NE (trade name), Rohm Pharma), etc.

Two or more of the above-described coating base materials may be mixed and used at an appropriate ratio. Further, when coating, a sunscreen such as titanium oxide, iron sesquioxide, etc., may be used.

The solid pharmaceutical preparation of the present invention can be safely administered orally to mammals (e.g., mice, rats, rabbits, cats, dogs, bovines, horses, monkeys and humans).

The dosage of the solid pharmaceutical preparation varies according to a particular basic medicinal component having an unpleasant taste, a subject, diseases, etc., but may be selected within such a range that an effective amount of a basic medicinal component having an unpleasant taste can be administered.

For example, when a basic medicinal component having an unpleasant taste is pioglitazone hydrochloride, the solid pharmaceutical preparation of the present invention is useful for prevention and/or treatment of diabetes. The dosage of the solid pharmaceutical preparation is, in terms of pioglitazone hydrochloride, 7.5 to 60 mg/day, preferably 15 to 60 mg/day per an adult (body weight: 60 kg), and this amount may be administered by dividing into 2 to 3 times a day.

In case that the solid pharmaceutical preparation of the present invention is a solid pharmaceutical preparation disintegrating in the oral cavity, the solid pharmaceutical preparation can be ingested without water or with an appropriate amount of water. Further, the solid pharmaceutical preparation can be ingested without disintegrating in the oral cavity.

Hereinafter, the "quickly disintegrating solid pharmaceutical preparation containing a medicinal component, a sugar alcohol and carboxymethylcellulose" will be described in detail.

The medicinal component may be solid, crystalline, oily, solution, and the like. Examples of-the medicinal component include nourishing and health-promoting agents, antipyretic analgesic antiphlogistic agents, psychotropics, antianxiety agents, antidepressants, hypnotic-sedatives, antispasmodics, central nervous system affecting drugs, cerebral metabolism improving agents, cerebral circulation activators, antiepileptic drugs, sympathomimetic agents, gastrointestinal function conditioning agents, antacids, antiulcer drugs, antitussive-expectorants, antiemetic drugs, respiratory stimulants, bronchodilators, antiallergic agents, agents for dental and oral use, antihistamines, cardiotonics, antiarrhythmics, diuretics, hypotensors, vasoconstrictors, coronary vasodilators, peripheral vasodilators, antihyperlipidemic agents, cholagogues, antibiotics, chemotherapeutic agents, agents for treating diabetes, drugs for osteoporosis, skeletal muscle relaxants, antirheumatics, hormone drugs, alkaloidal narcotics, sulfa drugs, antipodagric drugs, anticoagulants, anti-malignant tumor agents, etc. Two or more of these medicinal components may be mixed and used at an appropriate ratio unless such mixture adversely influences the pharmacological activity of each medicinal component.

Examples of the nourishing and health-promoting agent include vitamins such as vitamin A, vitamin D, vitamin E (e.g., D-alpha-tocopherol acetate), vitamin $B_1$ (e.g., dibenzoylthiamine, fursultiamine hydrochloride), vitamin $B_2$ (e.g., riboflavin tetrabutyrate), vitamin $B_6$ (e.g., pyridoxine hydrochloride), vitamin C (e.g., ascorbic acid, sodium L-ascorbate), vitamin $B_{12}$ (e.g., hydroxocobalamin acetate, cyanocobalamin); minerals such as calcium, magnesium and iron; proteins; amino acids; oligosaccharides; galenicals, etc.

Examples of the antipyretic analgesic antiphlogistic agent include aspirin, acetaminophen, ethenzamide, ibuprofen, diphenhydramine hydrochloride, diphenhydramine salicylate, diphenhydramine tannate, dl-chlorpheniramine maleate, dihydrocodeine phosphate, noscapine, methylephedrine hydrochloride, phenylpropanolamine hydrochloride, caffeine, anhydrous caffeine, serrapeptase, lysozyme chloride, tolfenamic acid, mefenamic acid, diclofenac sodium, flufenamic acid, salicylamide, aminopyrine, ketoprofen, indomethacin, bucolome, pentazocine, etc.

Examples of the psychotropic include chlorpromazine, reserpine, etc.

Examples of the antianxiety agent include alprazolam, chlordiazepoxide, diazepam, etc.

Examples of the antidepressant include imipramine, maprotiline hydrochloride, amphetamine, etc.

Examples of the hypnotic-sedative include estazolam, nitrazepam, diazepam, perlapine, phenobarbital sodium, etc.

Examples of the antispasmodic include meclizine hydrochloride, dimenhydrinate, scopolamine hydrobromide, papaverine hydrochloride, etc.

Examples of the central nervous system affecting drug include citicoline, etc.

Examples of the cerebral metabolism improving agent include meclofenoxate hydrochloride, donepezil hydrochloride, etc.

Examples of the cerebral circulation activator include vinpocetine, etc.

Examples of the antiepileptic drug include phenytoin, carbamazepine, etc.

Examples of the sympathomimetic agent include isoproterenol hydrochloride, etc.

Examples of the gastrointestinal function conditioning agent include stomachic-digestives such as diastase, saccharated pepsin, scopolia extract, cellulase AP3, lipase AP, cinnamon oil; intestinal function controlling drugs such as berberine chloride, resistant lactic acid bacterium, *Lactobacillus bifidus*; cetraxate hydrochloride, etc.

Examples of the antacid include magnesium carbonate, sodium hydrogen carbonate, magnesium aluminometasilicate, synthetic hydrotalcite, precipitated calcium carbonate, magnesium oxide, etc.

Examples of the antiulcer drug include lansoprazole, omeprazole, rabeprazole, famotidine, cimetidine, ranitidine hydrochloride, etc.

Examples of the antitussive-expectorant include cloperastine hydrochloride, dextromethorphan hydrobromide, theophylline, potassium guaiacolsulfonate, guaifenesin, codeine phosphate, phenylpropanolamine hydrochloride, bromhexine hydrochloride, ambroxol hydrochloride, etc.

Examples of the antiemetic drug include diphenidol hydrochloride, metoclopramide, etc.

Examples of the respiratory stimulant include levallorphan tartrate, etc.

Examples of the bronchodilator include theophylline, salbutamol sulfate, etc.

Examples of the antiallergic agent include amlexanox, seratrodast, isothipendyl hydrochloride, promethazine hydrochloride, promethazine methylenedisalicylate, clemastine fumarate, chlorpheniramine maleate, ketotifen fumarate, alimemazine tartrate, azelastine hydrochloride, emedastine difumarate, epinastine hydrochloride, ibudilast, oxatomide, etc.

Examples of the agent for dental and oral use include oxytetracycline, triamcinolone acetonide, chlorhexidine hydrochloride, lidocaine, etc.

Examples of the antihistamine include diphenhydramine hydrochloride, promethazine, isothipendyl hydrochloride, dl-chlorpheniramine maleate, etc.

Examples of the cardiotonic include caffeine, digoxin, etc.

Examples of the antiarrhythmic include procainamide hydrochloride, propranolol hydrochloride, pindolol, etc.

Examples of the diuretic include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), anti-aldosterone agents (e.g., spironolactone, triamterene), carbonic anhydrase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide, etc.

Examples of the hypotensor includes angiotensin converting enzyme inhibitors (e.g., delapril hydrochloride, captopril, enalapril), angiotensin II receptor antagonists (e.g., candesartan cilexetil, losartan, eprosartan, valsartan, telmisartan, irbesartan, tasosartan), calcium channel blockers (e.g., manidipine hydrochloride, nifedipine, amlodipine, efonidipine, nicardipine), potassium channel opener (e.g., levcromakalim, L-27152, AL 0671, NIP-121), clonidine, hydralazine hydrochloride, labetalol hydrochloride, methyldopa, etc.

Examples of the vasoconstrictor include phenylephrine hydrochloride, etc.

Examples of the coronary vasodilator include carbocromen hydrochloride, molsidomine, verapamil hydrochloride, etc.

Examples of the peripheral vasodilator include cinnarizine, etc.

Examples of the antihyperlipidemic agent include HMG-CoA reductase inhibitors (e.g., cerivastatin sodium, simvastatin, pravastatin sodium, fluvastatin sodium, atorvastatin, itavastatin, lovastatin), squalene synthase inhibitors, fibrate compounds (e.g., bezafibrate, clofibrate, simfibrate, clinofibrate), ACAT inhibitors (e.g., avasimibe, eflucimibe), anion-exchange resins (e.g., colestyramine), probucol, nicotinic acid derivatives (e.g., nicomol, niceritrol), ethyl icosapentate, phytosterols (e.g., soysterol, gamma-oryzanol), etc.

Examples of the cholagogue include dehydrocholic acid, torepibton, etc.

Examples of the antibiotic include cephem antibiotics such as cephalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil; synthetic antibacterials such as ampicillin, cyclacillin, nalidixic acid, enoxacin; monobactam antibiotics such as carumonam sodium; macrolide antibiotics such as erythromycin, clarithromycin, kitasamycin, josamycin, midecamycin, roxithromycin, azithromycin; penem antibiotics; carbapenem antibiotics, etc.

Examples of the chemotherapeutic agent include sulfamethizole, etc.

Examples of the agent for treating diabetes include insulin resistance improving agents (e.g., pioglitazone hydrochloride, troglitazone, rosiglitazone maleate, GI-262570, JTT-501, MCC-555, YM-440, KRP-297, CS-011, FK-614), alpha-glucosidase inhibitors (e.g., voglibose, acarbose, miglitol, emiglitate), biguanides (e.g., fenformin, metformin hydrochloride, buformin hydrochloride), insulin secretagogues [sulfonylurea drugs (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide, or calcium salt hydrate thereof, GLP-1], amyrin agonists (e.g., pramlintide), phosphotyrosinphosphatase inhibitors (e.g., vanadic acid), dipeptidyl peptidases IV inhibitors (e.g., NVP-DPP-278, PT-100, P32/98, LAF-237), beta3 agonists (e.g., CL-316243, SR-58611-A, UL-TG-307, SB-226552, AJ-9677, BMS-196085, AZ40140), gluconeogenesis inhibitors (e.g., glycogen phosphorylase inhibitor, glucose-6-phosphatase inhibitor, glucagon antagonist), SGLT(sodium-glucose cotransporter)inhibitor (e.g., T-1095), aldose reductase inhibitors (e.g., tolrestat, epalrestat, zenarestat, zopolrestat, minalrestat, fidarestat, SNK-860, CT-112), etc.

Examples of the drug for osteoporosis include alfacalcidol, calcitriol, elcaltonin, calcitonin-salmon, estriol, ipriflavone, pamidronate disodium, alendronate sodium hydrate, incadronate disodium, etc.

Examples of the skeletal muscle relaxant include methocarbamol, etc.

Examples of the antirheumatic include methotrexate, bucillamine, etc.

Examples of the hormone drug include liothyronine sodium, dexamethasone sodium phosphate, prednisolone, oxendolone, leuprorelin acetate, etc.

Examples of the alkaloid narcotic include opium, morphine hydrochloride, morphine sulfate, ipecac, oxycodone hydrochloride, opium alkaloid hydrochlorides, cocaine hydrochloride, etc.

Examples of the sulfa drug include sulfanilamide, sulfamethizole, etc.

Examples of the antipodagric include allopurinol, colchicine, etc.

Examples of the anticoagulant include dicoumarol, etc.

Examples of the anti-malignant tumor agents include 5-fluorouracil, uracil, mitomycin, etc.

Among them, preferred medicinal components are hypotensors, agents for treating diabetes, diuretics, etc., and more preferred are manidipine hydrochloride, voglibose, candesartan cilexetil, hydrochlorothiazide, pioglitazone hydrochloride, etc. In addition, examples of a preferred combination when using two ore more medicinal components together include a combination of a hypotensor and a diuretic (preferably, a combination of candesartan cilexetil and hydrochlorothiazide).

When each of the above-mentioned medicinal components forms a salt, it may also be used as free form thereof. When each of the above-mentioned medicinal components is free form that can form a salt, it may also be used as a salt. Such a salt include a pharmaceutically acceptable salt such as a salt formed with an inorganic base, a salt formed with an organic base, a salt formed with an inorganic acid, a salt formed with an organic acid, and a salt formed with a basic or acidic amino acid.

Preferred examples of the salt formed with an inorganic base include salts formed with alkali metals such as sodium, potassium; alkaline earth metals such as calcium, magnesium; and aluminum, ammonium and the like.

Preferred examples of the salt formed with an organic base include salts formed with trimethylamine, triethylamine, pyridine, picoline, ethanolamine, diethanolamine, triethanolamine, dicyclohexylamine, N,N-dibenzylethylenediamine and the like.

Preferred examples of the salt formed with an inorganic acid include salts formed with hydrochloric acid, hydrobromic acid, nitric acid, sulfuric acid, phosphoric acid and the like.

Preferred examples of the salt formed with an organic acid include salts formed with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt formed with a basic amino acid include salts formed with arginine, lysine, ornithine and the like. Preferable examples of the salt formed with an acidic amino acid include salts formed with aspartic acid, glutamic acid and the like.

The above-described medicinal component may be that diluted with a diluent generally used in the medical and food field. Further, the medicinal component may be coated with a coating agent as described hereinafter for masking a bitter taste, etc.

The content of the medicinal component in the quickly disintegrating solid pharmaceutical preparation of the present invention varies according to particular type and/or dose of that component, but is normally 0.01 to 40 parts by weight, preferably 0.01 to 20 parts by weight based on 100 parts by weight of the solid pharmaceutical preparation.

Examples of the sugar alcohol used in the quickly disintegrating solid pharmaceutical preparation of the present invention include those exemplified with respect to the above-mentioned solid pharmaceutical preparation.

Normally, the content of the sugar alcohol in the quickly disintegrating solid pharmaceutical preparation of the present invention is 5 to 97 parts by weight, preferably 10 to 90 parts by weight, more preferably 44 to 90 parts by weight based on 100 parts by weight of the solid pharmaceutical preparation.

Further, the solid pharmaceutical preparations having an excellent disintegration property can be obtained by using the sugar alcohol in an amount of 1 to 100 parts by weight, preferably 2 to 50 parts by weight based on 1 part by weight of carboxymethylcellulose.

Examples of carboxymethylcellulose used in the quickly disintegrating solid pharmaceutical preparation of the present invention include that exemplified with respect to the above-mentioned solid pharmaceutical preparation, and it is used in the same amount as that of the above-mentioned solid pharmaceutical preparation.

Examples of the dosage form of the quickly disintegrating solid pharmaceutical preparation of the present invention include tablets, granules, fine granules, pills, etc. Among them, tablets are preferred.

In the present invention, the "quickly disintegrating property" means such a property that the solid pharmaceutical preparation disintegrates within a short period of time (such as 5 to 90 seconds) in the oral cavity, in water or in stomach. While disintegration time of the quickly disintegrating solid pharmaceutical preparation of the present invention in the oral cavity (the time required for complete disintegration by saliva in the oral cavity of a healthy male or female adult) varies according to a dosage form and/or size of the quickly disintegrating solid pharmaceutical preparation, in case that the quickly disintegrating solid pharmaceutical preparation is in the form of a tablet, for example, the disintegration time is normally 5 to 90 seconds, preferably 5 to 60 seconds, more preferably 5 to 30 seconds.

The quickly disintegrating solid pharmaceutical preparation of the present invention is, more preferably, the solid pharmaceutical preparation quickly disintegrating in the oral cavity. The solid pharmaceutical preparation quickly disintegrating in the oral cavity is useful in prevention and treatment of various diseases as a preparation easy to ingest for patients having a difficulty in swallowing a drug, elderly persons, or children, and as a preparation safe in an emergency for general adults.

Hardness of the quickly disintegrating solid pharmaceutical preparation of the present invention (that measured by a tablet hardness tester) is, preferably 15 to 200 N, more preferably 15 to 150 N.

The quickly disintegrating solid pharmaceutical preparation of the present invention may contain additives conventionally used in the field of pharmaceuticals. Examples of such additives include excipients, disintegrants, binders, acidulants, foaming agents, artificial sweeteners, flavoring agents, lubricants, coloring agents, stabilizers, pH control agents, surfactants, corrigents, etc. Two or more thereof may be mixed and used at an appropriate ratio. Examples of these additives include those exemplified with respect to the above-mentioned solid pharmaceutical preparation, and they are used in an amount conventional in the field of pharmaceuticals. A particle size of the additive is not specifically limited, but preferably not more than 500 μm which produces little or no roughness in the oral cavity.

In addition, the quickly disintegrating solid pharmaceutical preparation of the present invention may contain additives such as a polyanionic polymer and a corrigent, etc. Two or more thereof may be mixed and used at an appropriate ratio.

In case that the medicinal component used in the present invention is a basic medicinal component having an unpleasant taste (such as bitter taste, hot taste, pungent taste, etc.), the quickly disintegrating solid pharmaceutical preparation in which the unpleasant taste of the medicinal component is masked can be obtained by using these additives.

Examples of the polyanionic polymer and the corrigent include those exemplified with respect to the above-mentioned solid pharmaceutical preparation, and they are used in the same amount as that of the above-mentioned solid pharmaceutical preparation.

The quickly disintegrating solid pharmaceutical preparation of the present invention can be manufactured, for example, according to a conventional method in the field of pharmaceuticals, by mixing the medicinal component, the sugar alcohol and carboxymethylcellulose optionally together with the above-described additives and then compression-molding. Mixing (includes granulation, drying, milling, etc.) and compression molding are carried out according to the same manner as that of the above-described solid pharmaceutical preparation.

The quickly disintegrating solid pharmaceutical preparation of the present invention can also be manufactured by mixing a composition comprising the medicinal component and the sugar alcohol (hereinafter, referred to as composition Aa) and a composition comprising the sugar alcohol and carboxymethylcellulose (hereinafter, referred to as composition Bb) and compression-molding the resultant mixture.

The sugar alcohol contained in the above-described compositions Aa and Bb may be the same or different. Further, these compositions may contain the above-described additives. The content of each component in compositions Aa and Bb can be determined appropriately so that the content of each component in the desired quickly disintegrating solid pharmaceutical preparation is the above-mentioned content.

Examples of a preferred manufacturing process of the quickly disintegrating solid pharmaceutical preparation of the present invention includes the following processes.

The medicinal component, the sugar alcohol and carboxymethylcellulose are mixed, optionally together with above-mentioned additives, in an appropriate mixer, and the mixture is granulated, followed by tableting with an appropriate tableting machine to obtain tablets.

Granulation is carried out by compressing and granulating the mixture in dry granulation, for example, with a slug process or a roller compactor process; or by wet granulating using a solvent (e.g., water, acetone, ethyl alcohol, propyl alcohol, a mixture thereof, etc.) in which the above-mentioned binder is dissolved or dispersed as needed; etc.

In the quickly disintegrating solid pharmaceutical preparation of the present invention, in case of using the polyanionic polymer such as sodium carboxymethylcellulose, sodium alginate, etc., the solid pharmaceutical preparation having an excellent disintegration property can be obtained by mixing a composition comprising the medicinal component, the sugar alcohol and the polyanionic polymer (hereinafter, referred to as composition Cc) and a composition comprising the sugar alcohol and carboxymethylcellulose (hereinafter, referred to as composition Dd) and then compression-molding the resultant mixture. In the quickly disintegrating solid pharmaceutical preparation manufactured by this process, since strong binding power among particles in the preparation brought about by the polyanionic polymer is reduced, a disintegration property of the preparation is improved.

The sugar alcohols contained in compositions Cc and Dd described above may be the same or different. Further, these compositions may contain the above-described additives. The content of each component in compositions Cc and Dd is determined appropriately so that the content of each component in the desired quickly disintegrating solid pharmaceutical preparation is the above-mentioned content.

In case of using the polyanionic polymer, the following process can be exemplified as a preferred manufacturing process of the quickly disintegrating solid pharmaceutical preparation.

The medicinal component, the sugar alcohol and the polyanionic polymer are mixed optionally together with the above-described additives by an appropriate mixer, and the resultant mixture is granulated.

On the other hand, the sugar alcohol and carboxymethylcellulose are mixed optionally together with above-described additives by an appropriate mixer, and the resultant mixture is granulated.

The above two granules are mixed optionally together with the above-described additives and the resultant mixture is subjected to tableting by an appropriate tableting machine to give a tablet.

The quickly disintegrating solid pharmaceutical preparation of the present invention can be manufactured by coating fine granular cores with the medicinal component, the sugar alcohol, carboxymethylcellulose, and optionally the above-described additives according to a conventional method in the field of pharmaceuticals.

A shape of the quickly disintegrating solid pharmaceutical preparation of the present invention is not specifically limited and may be any of the form of round, caplet, doughnut, oblong, etc., and may be a multi-layer tablet, a nucleated tablet, etc.

The quickly disintegrating solid pharmaceutical preparation may be coated with a coating agent for masking taste and/or flavor, or for providing enteric abilities or sustained-release abilities, and may be putted a mark or a letter for identification, and further a cleavage line for partition. Examples of the coating base material include those exemplified with respect to the above-mentioned solid pharmaceutical preparation, and two or more thereof may be mixed and used at an appropriate ratio. Further, when coating, a sunscreen such as titanium oxide, iron sesquioxide, etc., may be used.

The quickly disintegrating solid pharmaceutical preparation of the present invention can be safely administered orally to mammals (e.g., mice, rats, rabbits, cats, dogs, bovines, horses, monkeys, humans, etc.).

The dosage of the quickly disintegrating solid pharmaceutical preparation varies according to a particular kind of the medicinal component, a subject, a particular kind of a disease, but may be selected within such a range that an effective amount of the medicinal component can be administered.

For example, when the medicinal component is pioglitazone hydrochloride, the quickly disintegrating solid pharmaceutical preparation of the present invention is useful for prevention and/or treatment of diabetes. The dosage of the quickly disintegrating solid pharmaceutical preparation is, in terms of pioglitazone hydrochloride, 7.5 to 60 mg/day, preferably 15 to 60 mg/day per an adult (body weight: 60 kg), and this amount may be administered by dividing into 2 to 3 times a day.

For example, when the medicinal component is manidipine hydrochloride, the quickly disintegrating solid pharmaceutical preparation of the present invention is useful for prevention and/or treatment of hypertension, etc. The dosage of the quickly disintegrating solid pharmaceutical preparation is, in terms of manidipine hydrochloride, 1 to 100 mg/day, preferably 5 to 20 mg/day per an adult (body weight: 60 kg), and this amount may be administered by dividing into 2 to 3 times a day.

For example, when the medicinal component is voglibose, the quickly disintegrating solid pharmaceutical preparation of the present invention is useful for prevention and/or treatment of obesity, adiposis, hyperlipemia, diabetes, etc. The dosage of the quickly disintegrating solid pharmaceutical preparation is, in terms of voglibose, 0.01 to 30 mg/day, preferably 0.1 to 3 mg/day per an adult (body weight: 60 kg), and this amount may be administered by dividing into 2 to 3 times a day.

For example, when the medicinal component is candesartan cilexetil, the quickly disintegrating solid pharmaceutical preparation of the present invention is useful for prevention and/or treatment of hypertension, cardiac disease, cerebral apoplexy, renal diseases, etc. The dosage of the quickly disintegrating solid pharmaceutical preparation is, in terms of candesartan cilexetil, 1 to 50 mg/day, preferably 2 to 30 mg/day per an adult (body weight: 60 kg), and this amount may be administered by dividing into 2 to 3 times a day.

When the quickly disintegrating solid pharmaceutical preparation of the present invention is the solid pharmaceutical preparation disintegrating in the oral cavity, the quickly disintegrating solid pharmaceutical preparation can be ingested without water or with an appropriate amount of water. Further, the quickly disintegrating solid pharmaceutical preparation can also be ingested without disintegrating in the oral cavity.

The present invention will be illustrated in detail by Examples and Test Examples. However, the present invention is not limited thereto.

EXAMPLES

Example 1

Pioglitazone hydrochloride (350 g), sodium carboxymethylcellulose (GOTOKU CHEMICAL) (150 g), D-mannitol (TOWAKASEI) (400 g) and low-substituted hydroxypropyl cellulose LH-30 (Shin-Etsu Chemical) (100 g) were placed in a high-speed stirring granulator (Powrex Corporation, FM-VG-10) and granulated with adding purified water (300 g) thereto. After granulation, the resultant was vacuum-dried to obtain granules (hereinafter referred to as granule A).

On the other hand, D-mannitol (1891.6 g), carboxymethylcellulose (GOTOKU CHEMICAL) (360 g) and sodium glutamate (Takeda Chemical Industries) (36 g) were placed in a fluidized bed granulation dryer (Powrex Corporation, FD-3SN type) and granulated with spraying purified water (778.3 g) containing D-mannitol (70.8 g). After granulation, the resultant was dried to obtain granules (hereinafter referred to as granule B).

Granule A (31.49 g), granule B (66.51 g), aspartame (AJINOMOTO) (1 g) and a sucrose fatty acid ester (Mitsubishi-Kagaku Foods) (2 g) were mixed.

The powder mixture obtained was compressed into tablets by using a tableting machine (SHIMADZU CORPORATION, Autograph AG-5000B, tablet size of 11.5 mm in diameter, compression force of 10 kN/cm$^2$) to obtain tablets each weighing 450 mg.

Example 2

The powder mixture obtained in Example 1 was compressed into tablets by using a tableting machine (SHIMADZU CORPORATION, Autograph AG-5000B, tablet size of 10.0 mm in diameter, compression force of 12.3 kN/cm$^2$) to obtain tablets each weighing 300 mg.

Example 3

D-mannitol (2226.7 g), carboxymethylcellulose (252 g), crystalline cellulose (Asahi Kasei) (108 g) and sodium glutamate (18 g) were placed in a fluidized bed granulation dryer (Powrex Corporation, FD-3SN type) and granulated with spraying purified water (886.2 g) containing D-mannitol (80.6 g). After granulation, the resultant was dried to obtain granules (hereinafter referred to as granule C).

Granule A obtained by Example 1 (23.61 g), granule C (74.59 g), aspartame (0.8 g) and a sucrose fatty acid ester (1 g) were mixed.

The powder mixture obtained was compressed into tablets by using a tableting machine (SHIMADZU CORPORATION, Autograph AG-5000B, tablet size of 9.0 mm in diameter, compression force of 14.7 kN/cm$^2$) to obtain tablets each weighing 200 mg.

Example 4

According to the same manner as that in Example 1, tablets were prepared except that sodium carboxymethylcellulose was replaced with sodium alginate (KIBUN FOOD CHEMIFA) and D-mannitol was replaced with erythritol (Nikken Chemicals).

Example 5

Pioglitazone hydrochloride (350 g), sodium carboxymethylcellulose (GOTOKU CHEMICAL) (88 g), D-mannitol (TOWAKASEI) (362 g) and low-substituted hydroxypropyl cellulose LH-30 (Shin-Etsu Chemical) (100 g) were placed in a fluidized bed granulation dryer (Powrex Corporation, FD-3SN) and granulated with spraying purified water (1000 g) containing D-mannitol (100 g). After granulation, the resultant was dried to obtain granules (hereinafter referred to as granule J).

On the other hand, D-mannitol (1600.4 g), carboxymethylcellulose (GOTOKU CHEMICAL) (350 g) and sodium glutamate (Takeda Chemical Industries) (70 g) were placed in a fluidized bed granulation dryer (Powrex Corporation, FD-3SN type) and granulated with spraying purified water (625 g) containing D-mannitol (62.5 g). After granulation, the resultant was dried to obtain granules (hereinafter referred to as granule K).

Granule J (31.49 g), granule K (59.51 g), aspartame (AJINOMOTO) (1.5 g), Silysia 320 (brand name, Fuji Silysia Chemical) (5 g), strawberry durrarohm (FIRMENICH) (0.5 g) and a sucrose fatty acid ester (2 g) were mixed.

The powder mixture obtained was compressed into tablets by using a tableting machine (SHIMADZU CORPORATION, Autograph AG-5000B, tablet size of 11.5 mm in diameter, compression force of 10 kN/cm$^2$) to obtain tablets each weighing 450 mg.

Example 6

Manidipine hydrochloride (60 g), lactose (Freund Inc.) (180.6 g), corn starch (Nihon Corn Starch) (9 g) and low-substituted hydroxypropyl cellulose LH-31 (Shin-Etsu Chemical) (45 g) were placed in a fluidized bed granulation dryer (Powrex Corporation, LAB-1 type) and granulated with spraying purified water (100 g) containing hydroxypropyl cellulose (NIPPON SODA) (6 g). After granulation, the resultant was dried to obtain granules (hereinafter referred to as granule D).

On the other hand, D-mannitol (256.5 g), carboxymethylcellulose (60 g) and crystalline cellulose (18 g) were placed in a fluidized bed granulation dryer (Powrex Corporation, LAB-1 type) and granulated with spraying purified water (100 g) containing D-mannitol (10 g). After granulation, the resultant was dried to obtain granules (hereinafter referred to as granule E).

Granule D (40.08 g), granule E (57.42 g), aspartame (1 g) and magnesium stearate (TAIHEI CHEMICAL INDUSTRIAL) (1.5 g) were mixed.

The powder mixture obtained was compressed into tablets by using a tableting machine (SHIMADZU CORPORATION, Autograph AG-5000B, tablet size of 9.5 mm in diameter, compression force of 10 kN/cm$^2$) to obtain tablets each weighing 250 mg.

Example 7

Lactose (400 g) was placed in a fluidized bed granulation dryer (Powrex Corporation, LAB-1 type) and granulated with spraying purified water (100 g) containing hydroxypropyl cellulose (4 g) and voglibose (4 g). After granulation, the resultant was dried to obtain granules (hereinafter referred to as granule F).

On the other hand, D-mannitol (246.6 g), carboxymethylcellulose (40 g) and crystalline cellulose (12 g) were placed in a fluidized bed granulation dryer (Powrex Corporation, LAB-1 type) and granulated with spraying purified water (100 g) containing D-mannitol (10 g). After granulation, the resultant was dried to obtain granules (hereinafter referred to as granule G).

Granule F (20.35 g), granule G (77.15 g), aspartame (1 g) and of magnesium stearate (1.5 g) were mixed.

The powder mixture obtained was compressed into tablets by using a tableting machine (SHIMADZU CORPORATION, Autograph AG-5000B, tablet size of 9.0 mm in diameter, compression force of 14.7 kN/cm$^2$) to obtain tablets each weighing 200 mg.

Example 8

Candesartan cilexetil (40 g), erythritol (Nikken Chemicals) (250 g) and corn starch (15 g) were placed in a fluidized bed granulation dryer (Powrex Corporation, LAB-1 type) and granulated with spraying purified water (120 g) containing hydroxypropyl cellulose (10 g). After granulation, the resultant was dried to obtain granules (hereinafter referred to as granule H).

On the other hand, D-mannitol (227.2 g), carboxymethylcellulose (40 g) and crystalline cellulose (12 g) were placed in to a fluidized bed granulation dryer (Powrex Corporation, LAB-1 type) and granulated with spraying purified water (100 g) containing D-mannitol (10 g). After granulation, the resultant was dried to obtain granules (hereinafter referred to as granule I).

Granule H (25.2 g), granule I (72.3 g), aspartame (1 g) and magnesium stearate (1.5 g) were mixed.

The powder mixture obtained was compressed into tablets by using a tableting machine (SHIMADZU CORPORATION, Autograph AG-5000B, tablet size of 9.5 mm in diameter, compression force of 14.7 kN/cm$^2$) to obtain tablets each weighing 250 mg.

Comparative Example 1

According to the same manner as that of Example 1, tablets were prepared except that sodium carboxymethylcellulose was replaced with D-mannitol.

Comparative Example 2

According to the same manner as that of Example 3, tablets were prepared except that sodium carboxymethylcellulose was replaced with D-mannitol.

Test Example 1

Determination of bitter taste of the tablets obtained by the above-described Examples and Comparative Examples were carried out by the following test method. The results are shown in Table 1.

(1) Determination of bitter taste

Three healthy adult males determined a bitter taste when disintegrating the tablet in the oral cavity according to the following criteria.

−: no or little unpleasant or bitter taste
+: an unpleasant or bitter taste.
++: a strong unpleasant or bitter taste

TABLE 1

| Tablets | bitter taste |
| --- | --- |
| tablet of Example 1 | − |
| tablet of Example 2 | − |
| tablet of Example 3 | − |
| tablet of Example 4 | − |
| tablet of Example 5 | − |
| tablet of Comparative Example 1 | ++ |
| tablet of Comparative Example 2 | ++ |

As shown in table 1, in the solid pharmaceutical preparation of the present invention, an unpleasant taste of the basic medicinal component having an unpleasant taste was fully masked.

Test Example 2

Determinations of tablet hardness and disintegration time in the oral cavity of the tablets obtained in the above-described Examples and Comparative Examples were carried out according to the following test methods. Results are shown in Table 2.

(1) Hardness test

A tablet hardness tester (manufactured by Toyama Sangyo, Co. Ltd.) was used. The results shown were averages of 5 tablets.

(2) Disintegration time in the oral cavity

The time required for complete disintegration of a tablet only by saliva in the oral cavity of three healthy adult males was measured.

TABLE 2

| Tablets | Hardness (N) | Disintegration time in oral cavity (sec.) |
| --- | --- | --- |
| Tablet of Example 1 | 52 | 20 |
| Tablet of Example 2 | 63 | 17 |
| Tablet of Example 3 | 62 | 11 |

TABLE 2-continued

| Tablets | Hardness (N) | Disintegration time in oral cavity (sec.) |
|---|---|---|
| Tablet of Example 4 | 48 | 23 |
| Tablet of Example 5 | 78 | 28 |
| Tablet of Example 6 | 48 | 20 |
| Tablet of Example 7 | 51 | 16 |
| Tablet of Example 8 | 44 | 23 |
| Tablet of Comp. Example 1 | 32 | 143 |

As shown in table 2, the solid pharmaceutical preparation and the quickly disintegrating solid pharmaceutical preparation of the present invention have a quick disintegration property and appropriate preparation strength (tablet hardness).

INDUSTRIAL APPLICABILITY

In the solid pharmaceutical preparation of the present invention, the unpleasant taste of a basic medicinal component having an unpleasant taste can be satisfactorily masked and excellent properties such as quick disintegration, appropriate preparation strength and high storage stability over a long period of time, etc., can be achieved. Further, the solid pharmaceutical preparation of the present invention has excellent productivity.

According to the manufacturing process of the present invention, the desired solid pharmaceutical preparation can be manufactured by simple and easy operation in a high yield.

The quickly disintegrating solid pharmaceutical preparation of the present invention has excellent properties such as quick disintegration, appropriate preparation strength, high storage stability over a long period of time, etc. Further, the quickly disintegrating solid pharmaceutical preparation of the present invention has excellent productivity.

According to the manufacturing process of the present invention, the desired quickly disintegrating solid pharmaceutical preparations can be manufactured by simple and easy operation in a high yield.

The invention claimed is:

1. A solid pharmaceutical preparation in the form of a tablet comprising 1) pioglitazone hydrochloride, 2) 5 to 97 parts by weight of D-mannitol, 3) 1 to 50 parts by weight of sodium carboxymethylcellulose, 4) 0.1 to 15 parts by weight of sodium glutamate, and 5) carboxymethylcellulose, all parts by weight being based on 100 parts by weight of the solid pharmaceutical preparation, wherein the time for complete disintegration of the solid pharmaceutical preparation by human saliva in the oral cavity of a healthy adult ranges from 5 to 90 seconds.

2. The pharmaceutical preparation according to claim 1, wherein the time for complete disintegration ranges from 5 to 60 seconds.

3. The pharmaceutical preparation according to claim 2, wherein the time for complete disintegration ranges from 5 to 30 seconds.

4. A process for manufacturing a solid pharmaceutical preparation, which comprises the steps of mixing a composition comprising pioglitazone hydrochloride D-mannitol, and 1 to 50 parts by weight of sodium carboxymethylcellulose, and a composition comprising D-mannitol and 0.1 to 15 parts by weight of sodium glutamate, and then compression-molding the resultant mixture, the total amount of D-mannitol being 5 to 97 parts by weight and all parts by weight being based on 100 parts by weight of the solid pharmaceutical preparation, wherein the time for complete disintegration of the solid pharmaceutical preparation by human saliva in the oral cavity of a healthy adult ranges from 5 to 90 seconds.

* * * * *